US00PP13525P3

(12) United States Plant Patent
Fear

(10) Patent No.: US PP13,525 P3
(45) Date of Patent: Jan. 28, 2003

(54) BLACKBERRY PLANT NAMED 'PECOS'

(75) Inventor: Carlos D. Fear, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/772,211

(22) Filed: Jan. 29, 2001

(65) Prior Publication Data

US 2002/0144321 P1 Oct. 3, 2002

(51) Int. Cl.[7] ..... A01H 5/00
(52) U.S. Cl. ..... Plt./203

(58) Field of Search ..... Plt./203

*Primary Examiner*—Bruce R. Campell
*Assistant Examiner*—June Hwu
(74) *Attorney, Agent, or Firm*—Pennie & Edmonds LLP

(57) ABSTRACT

The present invention relates to a new and distinct cultivar of blackberry plant named 'Pecos'. The new cultivar is distinguished from other blackberry cultivars by its fruit of excellent fruit firmness and shipping quality. 'Pecos' is a thornless midseason cultivar. The new cultivar is distinguished from its seed parent by its earlier season, lower chill requirement, and greater vigor. The new cultivar is distinguished from its pollen parent by having firmer fruit and better fresh market shipping quality.

2 Drawing Sheets

LATIN NAME OF THE GENUS AND SPECIES OF THE PLANT CLAIMED

Rubus hybrid.

VARIETY DENOMINATION

'Pecos'.

1. BACKGROUND OF THE INVENTION

This invention relates to a new cultivar of blackberry called 'Pecos'. The new cultivar was developed from hybridization of the patented female selection 'Navaho', U.S. Plant Pat. No. 6,679, with the patented male cultivar 'Loch Ness', U.S. Plant Pat. No. 6,782. The parents were crossed in Spring 1991 whereafter fruit and seed were collected to produce seedlings for field planting in Watsonville, Calif. in 1991. The new cultivar was selected in July 1993 for its thornless canes and firm, attractive fruit. The cultivar was asexually propagated in Watsonville, Calif., and reproduced true to type plants by in vitro shoot tip culture, root sucker division, and root cuttings.

2. SUMMARY OF THE INVENTION

The present invention provides a new and distinct blackberry cultivar named 'Pecos'. The variety is botanically identified as Rubus L. subgenus Rubus. The variety is a complex Rubus hybrid, which can be characterized as an erect tetraploid with considerable *R. allegheniensis* background with other species such as *R. trivialis, R. argutus* and *R. ulmifolious* also appearing in its background. The new cultivar produces a floricane crop which begins in late June and continues until late August. The new blackberry variety is distinguished from other varieties by a number of characteristics as set forth in Table 1. In particular, the new cultivar is distinguished by its thornless canes, midsummer production, firm fruit and excellent shipping qualities. The fruit of 'Pecos' is medium glossy and medium-sized compared to other cultivars. It has a solid black color with minimal postharvest drupelet color reversion. There have been no observed plant or fruit diseases and no observed pest resistance or susceptibility. The variety has been developed for fresh market shipping use, and has performed well in coast-to-coast shipping tests and held up well after cold storage at 34 degrees Fahrenheit for periods of up to ten days.

3. COMPARISON TO SIMILAR VARIETIES

The varieties that we believe to be similar to 'Pecos' from those known to us are its parent varieties, 'Loch Ness' (U.S. Plant Pat. No. 6,782) and 'Navaho' (U.S. Plant Pat. No. 6,679). 'Pecos' is intermediate between its parents for many characteristics. 'Pecos' is particularly characterized by having more vigor and a lower chilling requirement than 'Navaho', and having firmer fruit that 'Loch Ness'. The season of ripening of 'Pecos' is similar to that of 'Loch Ness' and earlier than that of 'Navaho'.

4. BRIEF DESCRIPTION OF THE DRAWINGS

The accompanying photographs show typical specimens of the fruit, leaves and shoot of the new cultivar, in color as nearly true as reasonably possible in color illustrations of this type.

5. DESCRIPTION OF THE NEW VARIETY

Figure 1:
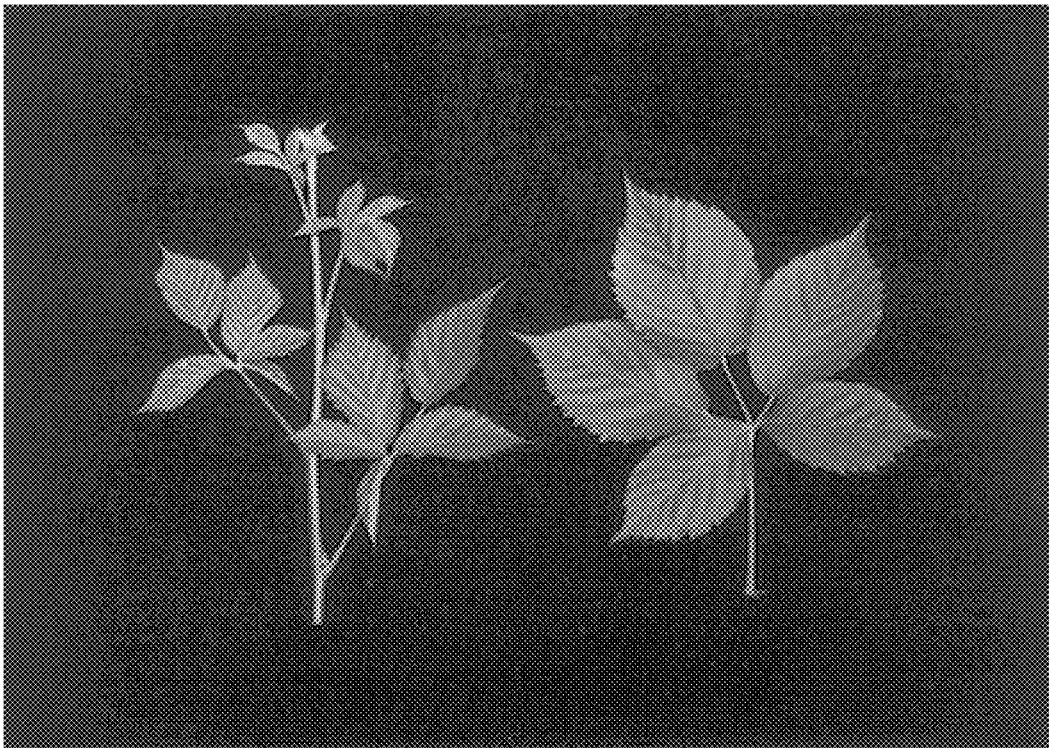
FIG. 1 is a photograph showing a primocane shoot and mature leaf of 'Pecos'.
Figure 2:
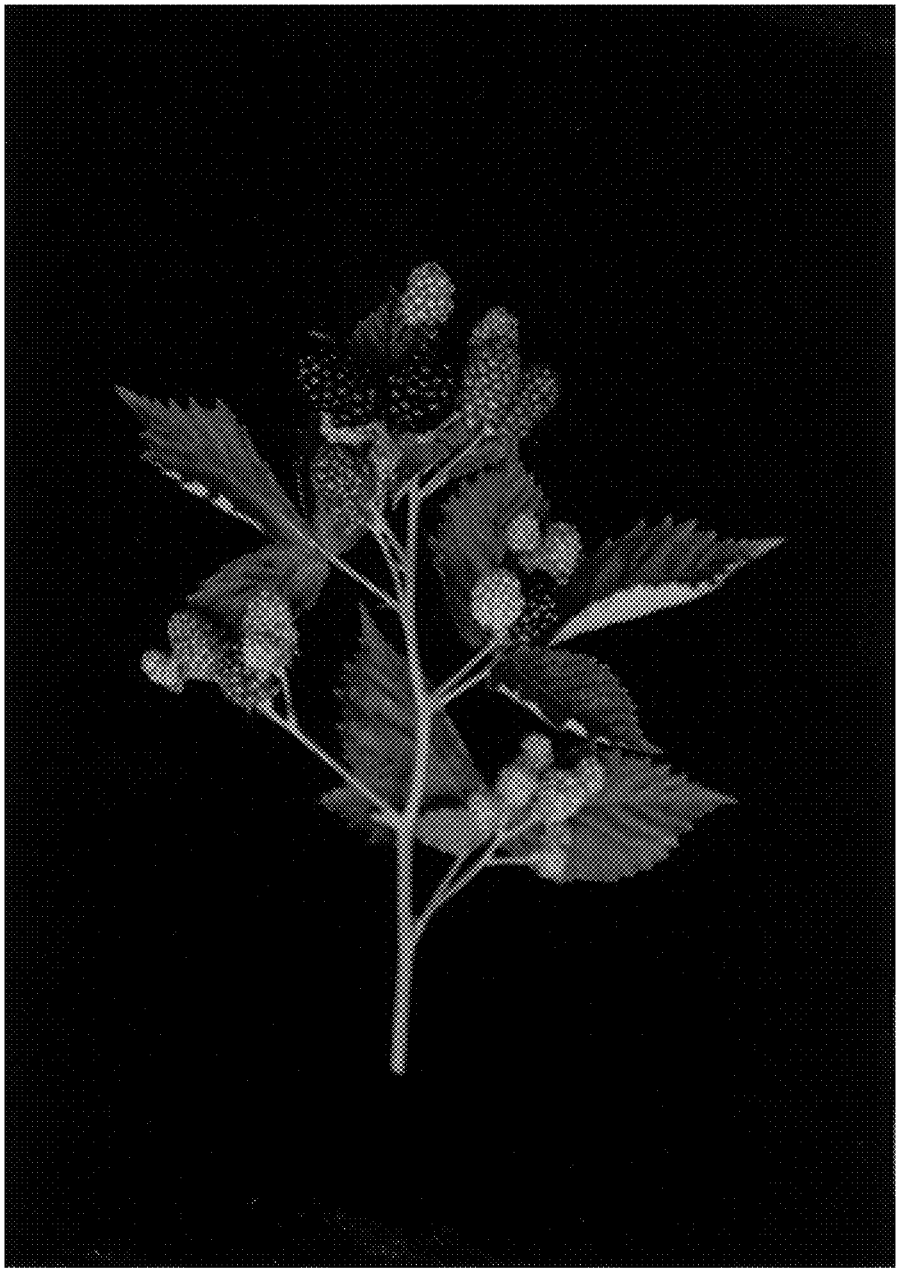
FIG. 2 is a photograph showing a 'Pecos' fruiting lateral with fruit in various stages of development.

The following detailed description of the new blackberry cultivar, 'Pecos', is based upon recorded observations of plants two to five years old grown using commercial growing practices in Watsonville, Calif., and is believed to apply to plants of the 'Pecos' cultivar grown in similar conditions of soil and climate elsewhere. Plants were planted on soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

5.2 CHARACTERISTICS OF THE NEW VARIETY

Table 1 provides information on the plant and fruit characteristics of the new blackberry cultivar 'Pecos' compared with characteristics of the blackberry cultivars 'Olallie' (non-patented) and 'Chester' (non-patented). Both 'Olallie' and 'Chester' are currently important cultivars for fresh market shipping, and thus are comparable to the proposed use of the new invention, 'Pecos'.

The new blackberry cultivar is particularly characterized and distinguished from other cultivars by its fruit of excellent fruit firmness and shipping quality. Flavor of 'Pecos' has been rated superior to many other cultivars in sensory tests.

Canes of 'Pecos' are thornless and moderately vigorous. The average cane length for 'Pecos' under a normal growing season is 5.75 feet and the average cane length for 'Chester' is 9 feet. The primocane color on the exposed side of the cane is 187B and 146B on the shaded side. Floricanes are 187B on the exposed side and 146B on the shaded sided.

The fruit yield of 'Pecos' is medium, averaging around 11,000 lbs per acre in comparison to the fruit yield of 'Olallie' which averages around 21,000 lbs per acre.

The leaf of 'Pecos' has very minor undulations between where the veins are and is nearly flat. The leaf surface of 'Pecos' has a few small, soft hairs on both the upper and lower leaf surface.

The petiole color is 187B when exposed to full sun. The bud break of 'Pecos' is in early April and usually 1–2 weeks before 'Chester'. The petal color of 'Pecos' is N155B. The pedicel length averages 14 mm under normal growing conditions. The sepal color is 139C.

'Pecos' is distinguished from its pollen parent, 'Loch Ness', by having firmer fruit with better fresh market shipping quality. 'Pecos' is distinguished from its seed parent, 'Navaho' by its earlier season, lower chill requirement and greater vigor.

TABLE 1

PLANT CHARACTERISTICS OF 'PECOS'

| | 'Pecos' | 'Olallie' | 'Chester' |
|---|---|---|---|
| GENERAL | | | |
| Vigor | moderate | moderate-high | high |
| Growth habit | semi-upright | trailing | semi-upright |
| Productivity | medium | high | high |
| Self fruitfulness | yes | yes | yes |
| Number of young shoots | few | medium | medium |
| CANES | | | |

TABLE 1-continued

PLANT CHARACTERISTICS OF 'PECOS'

| | 'Pecos' | 'Olallie' | 'Chester' |
|---|---|---|---|
| Primocanes | | | |
| Anthocyanin coloration | absent | present | present |
| Spines | absent | present | absent |
| color | — | purple | — |
| attitude of tip | — | horizontal | — |
| texture | — | heavy | — |
| presence and distribution on petioles | absent | present; irregularly distributed | absent |
| density in central third of shoot | — | medium | — |
| Internodal distance (cm)-central third of mature cane | 2.9 | 2.6 | 3.1 |
| Glaucosity on full grown shoot | absent or very weak | weak | weak |
| Strength of full grown shoot | strong | medium | strong |
| Cane cross section | angular to grooved | rounded to angular | angular to grooved |
| LEAVES | | | |
| Relief between veins | medium | medium | medium |
| Number of leaflets | sometimes 3 sometimes 5 | usually 3 | usually 5 |
| Leaf color | medium | medium | light |
| upper side | 137A, 147A | 137A, 137B | 147A |
| underside | 146A, 147B | 147B | 146A |
| Glossiness of upper surface | medium to glossy | medium | dull |
| Leaf cross section | concave | concave-flat | concave |
| Terminal leaflet | | | |
| length (cm) | 11 | 8.9 | 11.1 |
| width (cm) | 8.8 | 7.6 | 9 |
| shape | cordate | cordate | cordate |
| tip | acuminate | acuminate | acuminate |
| base | cordate | cordate | cordate |
| margin | double serrate | double serrate | double serrate |
| Lateral leaflet | | | |
| overlap of lateral leaflets | overlapping | overlapping | overlapping |
| length (cm) | 10.6 | 8.7 | 10.2 |
| width (cm) | 7.4 | 6.1 | 7.1 |
| shape | ovate | ovate | ovate |
| tip | acuminate | acuminate | acute |
| base | acute | acute | acute |
| margin | double serrate | double serrate | serrate |
| Petiole | | | |
| mean length (cm) | 7.9 | 5.3 | 7.9 |
| range | 3.7–12.5 | 3.6–8.7 | 3.9–10.2 |
| pigmentation of upper surface | light reddish | green-slightly pink | purple |
| pigmentation of underside | green | green-slightly pink | green-pinkish |
| Length of stalklet | short | very short | medium |
| Rachis length (cm) between terminal and adjacent lateral leaflets) | 3 | 2.8 | 3.1 |
| Stipule orientation | erect | variable; clasping to erect | erect |
| FLOWERS | | | |
| Time of bud burst | late | early | late |
| Time of beginning of flowering | medium | early | late |
| Flower size | medium-large | small to medium | small to medium |
| Petal size | | | |
| length (mm) | 20.3 | 16.5 | 18.3 |

TABLE 1-continued

| PLANT CHARACTERISTICS OF 'PECOS' | 'Pecos' | 'Olallie' | 'Chester' |
|---|---|---|---|
| width (mm) | 14.7 | 11.7 | 10.9 |
| Anthocyanin color of pedicel | absent | absent | present |
| Intensity of pedicel coloration | — | — | weak |
| Length of pedicel | short | long | short |
| Flower number (third node from tip of lateral) | 0.95 | 3.6 | 2 |
| FRUIT | | | |
| Harvest season | mid | early | mid to late |
| Dimensions | 4.5 | 5.2 | 3.2 |
| weight (g/fruit) | | | |
| Size | medium | medium | small |
| length (cm) | 2.1 | 3.3 | 1.9 |
| width (cm) | 1.8 | 1.4 | 1.9 |
| Fruiting lateral length (in mid cane) | short | medium | medium-long |
| mean number of fruit per lateral | 7.2 | 6.2 | 22.8 |
| range | 4–9 | 3–9 | 17–40 |
| Shape | ovate to elliptic; longer than broad | narrow ovate; much longer than broad | round to ovate; as long as broad |
| Color | black | purple-black to black | black |
| immature | 187A | 178A–183B | 184A |
| maturing | 187A | 187A | 200A–202A |
| mature | 202A | 200A | 202A |
| Firmness | very firm | medium | firm |
| Glossiness | medium | medium-strong | medium |
| Soluble solids | 10.8 | 9.7 | 9.9 |
| Titratable acidity (% as citric acid) (ml of added 0.1 N NaOH to pH 8.1) | 10.6 | 13.3 | 9.9 |
| Number of drupelets per fruit | 60 | 86 | 40 |

Table 2 provides information on the seed weight of the new blackberry cultivar 'Pecos' compared with characteristics of the blackberry cultivars 'Zorro' (application Ser. No. 09/772,327), 'Olallie' (non-patented), 'Chester' (non-patented), 'Sleeping Beauty' (application Ser. No. 09/772,329), and 'Sonoma'.

TABLE 2

| Cultivar | Seed Weight |
|---|---|
| 'Zorro' | 2.3 mg |
| 'Olallie' | 2.1 mg |
| 'Chester' | 3.5 mg |
| 'Sleeping Beauty' | 4.1 mg |
| 'Pecos' | 3.5 mg |
| 'Sonoma' | 3.4 mg |

5.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of 'Pecos', 'Chester', and 'Olallie' yielded DNA fragment patterns that uniquely distinguish each of these genetically distinct genotypes.

I claim:

1. A new and distinctive cultivar of blackberry plant, substantially as shown and described.

* * * * *